US00PP08142P

United States Patent [19]

Austin

[11] Patent Number: Plant 8,142

[45] Date of Patent: Feb. 16, 1993

[54] ROSE PLANT—'AUSFIN'

[75] Inventor: David C. H. Austin, Albrighton, England

[73] Assignee: David Austin Roses, Wolverhampton, England

[21] Appl. No.: 623,307

[22] Filed: Dec. 6, 1990

[51] Int. Cl.[5] ..... A01H 5/00

[52] U.S. Cl. ..... Plt./1

[58] Field of Search ..... Plt./1, 22, 26, 27

*Primary Examiner*—Howard J. Locker

*Attorney, Agent, or Firm*—Ladas & Parry

[57] ABSTRACT

A new variety of rose plant of the shrub class distinctive in its character by its fully double, pure pink flowers with abundant continual blooming, and the unusual shaping of the flowers.

1 Drawing Sheet

BACKGROUND OF THE INVENTION

The present invention relates to a new and distinct variety of shrub roses, said new variety originating as a single seeding resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof.

BRIEF DESCRIPTION OF THE DRAWING

The accompanying illustration shows typical cultivar flowers of this new cultivar in various stages of development, depicted in color nearly true as is possible to make the same in color illustrations of this character.

DETAILED BOTANICAL DESCRIPTION

The following is a detailed description of the new variety, terminology being in accordance with the "Methuen Handbook of Colour" published by Eyre Methuen Ltd (1963).

Variety denomination (in accordance with the UPOV Convertion): Ausfin.

*Cultivar.*—Financial Times Centenary.

*Type.*—Hardy, bush, outdoor, garden decoration.

*Class.*—Shrub.

Propagation: This variety holds its distinguishing characteristics through succeeding propagations by budding.

Asexual reproduction of the new cultivar by budding has taken place at a nursery in Albrighton, Nr. Wolverhampton; England and was derived as follows:

Female parent (seed parent): Un-named seedling (non-patented).

Male parent (pollen parent): Un-named seedling (non-patented).

The operation fo the artificial pollination is therefore expressed by the following: un-named seedling×un-named seedling (known to breeder as IMK×Susans Rose).

The following observations are made of specimens grown outdoors in England.

Plant Description

Plant:

*Height.*—135 cm.

*Habit.*—Upright, strong, and tall.

Branches:

*Young stems.*—Color: 20EB Parrot green with violet brown blush 10E6. Texture: Smooth with thorns and red glandular hairs. Thorns: 2-5 per internode.

*Old stems.* Color: 29F7 Dark green with extensive violet brown blush 10E6. Texture: Smooth with many red glandular hairs and thorns 3-15 per internode, basal width 2.8 mm, height 2.6 mm. Thorns: 3-15 per internode, basel width 2.8 mm height 2.6 mm.

LEAVES

Stipules:

*Length.*—0.8-2.2 cm.

*Width.*—0.4-0.6 cm.

*Angle of wingtips to petiole.*—Variable but most often 45°.

*Color.*—30B5.

*Margins.*—Lined with red glandular hairs.

*Shape.*—Medium width.

Petiole:

*General description.*—Length: 8-9 cm. Upperside color: 29F8 Dark green. Groove/hairs/thorns: Sparse red glandular hairs along edge of the groove. Underside: 30B7 Yellowish green. Hair/thorns: Small thorns 1.5×1.5 cm 1-2 per internode. Leaflets: Number: 3-7 (mainly 5). Shape: Ovoid with cuspidate tip. Serration: Serrate. Texture: Tough and leathery.

*General effect of foliage.*—Medium density.

*Color.*—Young foliage: Upperside: 29F7 dark green. Underside: 29D/E6 Greyish green. Adult foliage: Upperside: 29F8 Dark green. Underside: 29E6/7 Greyish green.

INFLORESCENCE

Number of flowers per stem: 1-10 (average 6).

Peduncle:

*Length.*—2-4 cm.

*Color.*—30E8.

*Thorns/hairs.*—Sparse red glandular hairs.

Sepals:

Upperside color.—30E8 Parrot green.

*Outer margins.*—1-2 ensiform protruberances with red glandular hairs.

*Inner margins.*—Smooth and lined with white downy hairs.

*Underside color.*—30B6.

*Outside and inside texture.*—Tough and leathery.

*Sepal length.*—2.2-3.0 cm.

*Bud shape.*—Rounded with cuspidate tip before bud break.

*Length.*—2.5 cm. before bud break.

*Max. width.*—1.5 cm. before bud break.

*Color when opening.*—11B7 Fraise.

*Flower shape.*—As a flattened cup.

*Diameter.*—7.0 cm.

*Flower color when opening.*—Upperside: 11A7 Geranium. underside: 10 B6 Greyish red.

*Flower color when blooming.*—Upperside: 12A5 Pink. Underside: 12A4 Pink.

*Flower coloring when finished blooming.*—Upperside: Outer petals: 13A3 Pink. Inner petals: 13A5. Underside: Outer petals: 13A2 Pinkish white inner petals: 13A4.

Length of blooming season at production location: From: June to October.

Fragrance: Good, sweet old fashioned.

Lasting quality: very good. Range in number of days on plant is 10-14 days. Range in number of days as cut flowers in 9-12 days.

Petals:

Shape.—outside: Very round, concave, base with slight shoulder apex slightly irregular, length 4.0-4.5 cm/width 3.5-4.0 cm. Inside: Slender, ovoid, top and rounded, irregular inner petals stamenoid base, v-shaped. Length 2.5-3.0 cm/width 1.5-2.0 cm. Middle: Ovoid, rounded top, base v-shaped. Length 3.5 cm/width 3 cm.

*Texture.*—Soft.

*Number.*—120-140.

*Cleaning.*—Average, the petals fall reasonably well but not as quickly as they should do.

Stamens:

*Number.*—110-120.

*Anthers.*—4A7 Reddish yellow.

*Filaments.*—8-10 mm 4A6 Reddish yellow.

Pistils:

*Number.*—170-180.

*Stigmas.*—Normal 3A4 pastel yellow.

*Styles.*—5-10 mm 1A3 Pale yellow may have cerise 12C8 blush towards apex.

Receptacle:

*Color.*—30C7.

*Texture.*—Smooth.

*Size.*—Width 1.1-1.4 cm. Length 1.0-1.2 cm.

*Shape.*—Cup shaped.

THE DEVELOPMENT

Vegetation: Vigorous.

Blooming: Abundant and continual.

Aptitude to bearing fruits: None.

Resistance to frost: Good.

Resistance to disease: Good.

I claim:

1. A new and distinct variety of rose plant of the shrub class, characterised as to novelty by its fully double flowers of a pure pink coloring, with abundant and continual blooming and the unusual shaping of the flower being substantially as shown and described.

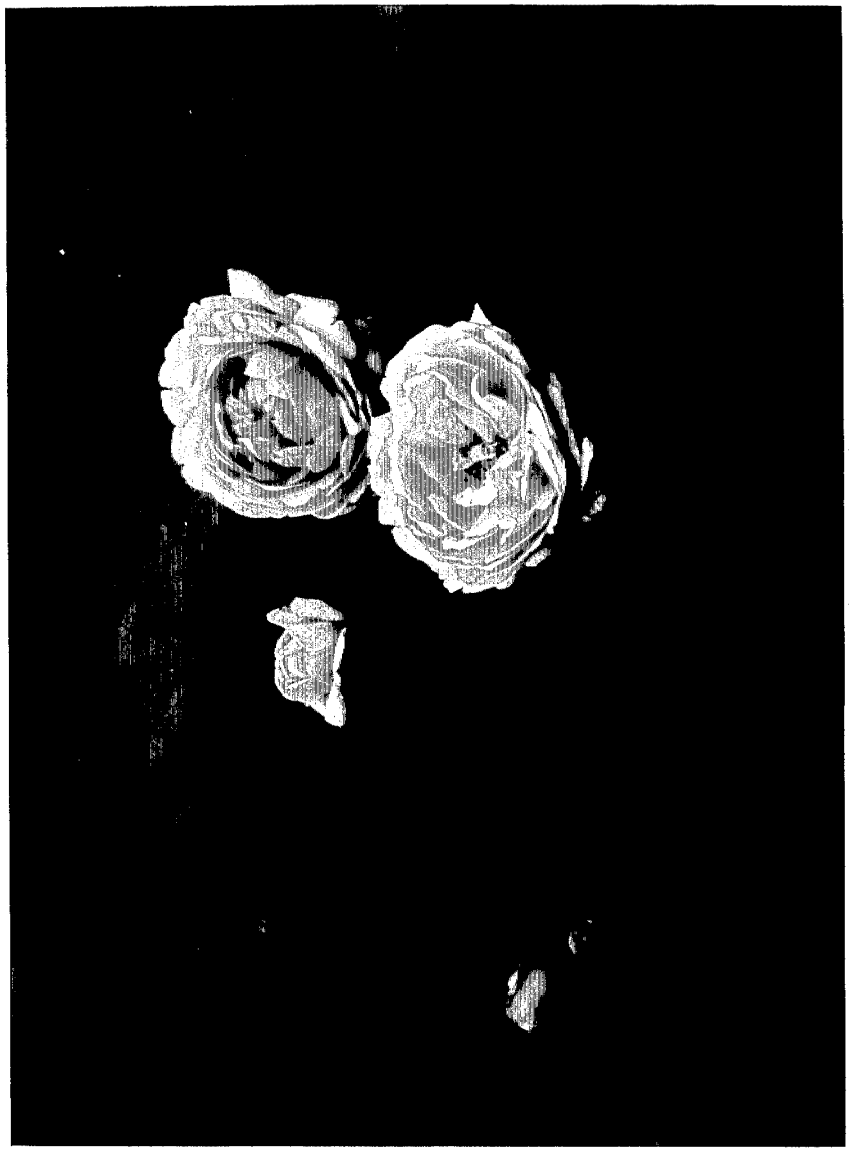

* * * * *